United States Patent
Imori et al.

(10) Patent No.: US 6,482,965 B2
(45) Date of Patent: Nov. 19, 2002

(54) MOLYBDENUM SOAP-CONTAINING METALLIC SOAP AND METHOD FOR PRODUCING THE SAME

(75) Inventors: Toru Imori, Toda (JP); Mizuho Yoshida, Toda (JP)

(73) Assignee: Japan Energy Corporation, Tokyo (JP)

( * ) Notice: Subject to any disclaimer, the term of this patent is extended or adjusted under 35 U.S.C. 154(b) by 56 days.

(21) Appl. No.: 09/813,758

(22) Filed: Mar. 21, 2001

(65) Prior Publication Data

US 2001/0016567 A1 Aug. 23, 2001

Related U.S. Application Data

(63) Continuation-in-part of application No. 09/402,848, filed as application No. PCT/JP99/02091 on Apr. 20, 1999, now abandoned.

(30) Foreign Application Priority Data

Apr. 21, 1998 (JP) .......................... 10-110762
Apr. 21, 1998 (JP) .......................... 10-110767

(51) Int. Cl.⁷ ................................ C07F 11/00
(52) U.S. Cl. .......................... 554/71; 554/124
(58) Field of Search .................. 554/71, 124

(56) References Cited

U.S. PATENT DOCUMENTS

| | | |
|---|---|---|
| 3,362,972 A | 1/1968 | Wallington |
| 3,578,690 A | 5/1971 | Becker |
| 5,994,434 A | 11/1999 | Uchino et al. |

FOREIGN PATENT DOCUMENTS

| | | |
|---|---|---|
| JP | 46-2497 | 1/1971 |
| JP | 51-40059 | 11/1976 |
| JP | 52-50768 | 12/1977 |
| JP | 61-215344 | 9/1986 |
| JP | 6-48978 | 2/1994 |
| JP | 6-219990 | 8/1994 |
| JP | 10-120615 | 5/1998 |
| JP | 10-287898 | 10/1998 |

Primary Examiner—Deborah Carr
(74) Attorney, Agent, or Firm—Flynn, Thiel, Boutell & Tanis, P.C.

(57) ABSTRACT

An object is to provide a homogeneous composite metallic soap containing molybdenum in high yields.

A composite metallic soap containing molybdenum is produced by reacting a fatty acid and a molybdenum compound under conditions where the fatty acid is in excess to synthesize a molybdenum soap and then adding a metal compound other than the molybdenum compound for reaction with the excess amount of fatty acid or by reacting a molybdenum compound and a fatty acid in the presence of a fatty acid and a metal compound that form a metallic soap having a softening point of 120° C. or less.

8 Claims, No Drawings

MOLYBDENUM SOAP-CONTAINING METALLIC SOAP AND METHOD FOR PRODUCING THE SAME

This application is a continuation-in-part of application Ser. No. 09/402,848, filed Oct. 7, 1999, which was the national stage of International Application No. PCT/JP99/02091, filed Apr. 20, 1999, which International Application published in Japanese.

TECHNICAL FIELD

The present invention relates to molybdenum soap-containing metallic soap used as an adhesive for accelerating the adhesion between a steel cord for radial tires and rubber, a hardener of unsaturated polyester resin, a hardening promoter for paints, a lubricant, a petroleum additive, catalysts for various chemical reactions and to a method for producing the same.

BACKGROUND ART

Metallic soaps containing cobalt or nickel as a principal metal are produced, for example, by a double decomposition method in which an aqueous sodium naphthenate solution and an aqueous metal sulfate solution are reacted, a direct method in which naphthenic acid and a metal salt are directly reacted, or the like.

However, upon synthesis of metallic soaps containing molybdenum as a principal metal, for example, molybdenum naphthenate, it is difficult to synthesize a fatty acid molybdenum soap in good yield since the reactivity between a metal salt, such as molybdenum trioxide, ammonium molybdate, or sodium molybdate that serves as a raw material for molybdenum, and a fatty acid is low, so that the following methods have been proposed.

The method in which a molybdenum compound and a monocarboxylic anhydride are reacted (Japanese Patent Application Laid-open No. 6-219990), The method in which acetic anhydride is used to obtain monocarboxylic acid molybdenum through the reaction between a molybdenum compound and a monocarboxylic acid (Japanese Patent Application Laid-open No. 6-48978).

The method in which molybdenic acid produced by a precipitation method is washed by water without drying and then reacted with a monocarboxylic acid under heating (Japanese Patent Publication No. 63-35616), The method in which an alkali metal salt of molybdenic acid, molybdenum halide, ammonium molybdate, molybdenum oxide and ammonia, or mixtures of these and a monocarboxylic acid are reacted at 100 to 300° C. (Japanese Patent Publication No. 52-50768), The method for producing an organic molybdenum compound in which a molybdenum acid salt obtained by reacting with hydrochloric acid in an aliphatic alcohol is reacted with an organic acid such as a higher fatty acid, naphthenic acid, or a resin acid under heating to a final state where the alcohol is absent (Japanese Patent Publication No. 46-2497), The method in which in the reaction between molybdenum and a carboxylic acid, molybdenum trioxide, oxalic acid, water and hexanoic acid are heated (Japanese Patent Publication No. 42-21326), and the like.

However, the molybdenum soaps obtained by these synthetic methods contain unreacted fatty acids. This is caused by the low reactivity between molybdenum and fatty acids and the occurrence of solidification as the reaction proceeds because the molybdenum soaps have high softening points. The unreacted fatty acids in many cases degrade the molybdenum soap-containing metallic soaps properties so that their presence is undesirable.

Furthermore, when composite metallic soaps constituted by a molybdenum soap and another metallic soap are produced, a metallic soap synthesized in a separate batch is to be mixed with the other molybdenum soap. In this case, although the fatty acids contained in the molybdenum soap are preferred from the viewpoint of mixing, the presence of fatty acids was a cause of a deterioration in the properties of composite metallic soaps as in the case of producing the molybdenum soap alone. On the other hand, since a decrease in the amount of unreacted fatty acid in the molybdenum soap results in solidification or production of a liquid having a high viscosity, it has been difficult to prepare a homogeneous composite metallic soap.

As described above, the above-described methods are insufficient from the viewpoint of producing a homogeneous composite soap constituted by a mixture of a molybdenum soap and another metallic soap in good yields and without remaining unreacted fatty acids, and no method has presently been found for economically producing a molybdenum soap-containing metallic soap that contains less by-products and has good storage stability.

DISCLOSURE OF THE INVENTION

Under the circumstances, an object of the present invention is to produce a homogeneous molybdenum soap-containing composite metallic soap in good yields.

The present inventors have made investigation with a view to developing a method for producing a homogeneous molybdenum soap-containing composite metallic soap in good yields, and as a result, they have now found that the production of a molybdenum soap under the conditions where a fatty acid is in excess and the addition of a metal compound to the resulting fatty acid-containing molybdenum soap for reaction with the fatty acid can readily produce a homogeneous molybdenum soap-containing composite metallic soap in high yields. Furthermore, they also found that as another embodiment, the synthesis of a molybdenum soap by reaction of a fatty acid and a molybdenum compound in the presence of a fatty acid and a metal compound that forms a metallic soap having a softening point of 120° C. or less, or in the presence of a metallic soap having a softening point of 120° C. or less, can readily produce a homogeneous molybdenum-containing composite metallic soap in high yields. Thus, the present invention has been completed based on the findings.

That is, the present invention is directed to:

(1) A method for producing a molybdenum soap-containing metallic soap, comprising the steps of reacting a fatty acid and a molybdenum compound under conditions where the fatty acid is in excess to synthesize a molybdenum soap and then adding an inorganic metal compound other than the molybdenum compound for reaction with the excess amount of fatty acid.

(2) The method for producing a molybdenum soap-containing metallic soap as described in (1) above, characterized in that no oxalic acid is added, and the fatty acid and the molybdenum compound are reacted directly at a fatty acid-to-molybdenum molar ratio of 3/1 or more to synthesize a fatty acid molybdenum soap.

(3) A molybdenum soap-containing metallic soap, characterized in that a molybdenum soap and a metallic soap other than the molybdenum soap contain the same fatty acid.

(4) A method for producing a molybdenum soap-containing metallic soap, comprising the steps of reacting a molybdenum compound and a fatty acid in the presence of a fatty acid and an inorganic metal compound other than molybdenum compound that form a metallic soap having a softening point of 120° C. or less.

(5) A method for producing a molybdenum soap-containing metallic soap, comprising the steps of synthesizing a molybdenum soap in the presence of a metallic soap having a softening point of 120° C. or less.

(6) The method for producing a molybdenum soap-containing metallic soap as described in (4) or (5) above, comprising the steps of synthesizing the molybdenum soap without addition of any oxalic acid.

(7) The method for producing a molybdenum soap-containing metallic soap as described in (4) or (5) above, characterized in that the atomic ratio of the molybdenum to the inorganic metal other than molybdenum, which are contained in the molybdenum soap-containing metallic soap, is ½ or less.

(8) A molybdenum soap-containing metallic soap, characterized by containing a metallic soap other than a molybdenum soap, having a softening point of 120° C. or less.

BEST MODE FOR CARRYING OUT THE INVENTION

Now, a first embodiment of the present invention will be explained.

The fatty acid as referred to herein means natural or synthetic, saturated or unsaturated fatty acids having a principal chain having from 6 to 30 carbon atoms or mixtures thereof. Specific examples thereof include caproic acid, caprylic acid, capric acid, lauric acid, myristic acid, palmitic acid, stearic acid, isostearic acid, arachic acid, behenic acid, oleic acid, linoleic acid, linolenic acid, ricinoleic acid, 12-hydroxystearic acid, dimeric acid, tallate, naphthenic acid, neodecanoic acid, a resin acid or natural oil and fat fatty acids containing these as main components, for example, fish oil hardened fatty acids, beef tallow hardened fatty acids, etc.

The molybdenum compound that can be used includes molybdenum oxide, ammonium molybdate, sodium molybdate, molybdenum acetylacetonate, etc.

The molybdenum soap is a soap that can be formed from the above-described fatty acids and molybdenum and specific examples thereof include molybdenum naphthenate, molybdenum neodecanoate, molybdenum resinate, etc.

As the metal compound other than the molybdenum compound can be used oxides, hydroxides, carbonates, alkoxides, organometallic compounds, etc. of metals such as magnesium, calcium, strontium, barium, zinc, cadmium, nickel, titanium, aluminum, etc. More specifically, zinc oxide, magnesium oxide, nickel carbonate, zinc hydroxide, etc. can be mentioned. Two or more of them may be used in combination. To synthesize a homogeneous molybdenum-containing metallic soap with good reactivity, metal species that produce a metallic soap having a low softening point are preferred and more particularly, use of a zinc compound is preferred.

The molybdenum soap-containing metallic soap that can be produced according to the first embodiment of the present invention includes those compounds in which the molybdenum soap is synthesized under the conditions where the fatty acid is in excess and the other metallic soaps other than the molybdenum soap also contain a metallic soap that comprises the same fatty acid moiety as that contained in the molybdenum soap so that the excess amount of fatty acid and the metal compound other than the molybdenum compound can be reacted. Examples of such molybdenum soap-containing metallic soap include Zn naphthenate/Mo naphthenate, Zn neodecanoate/Mo neodecanoate, Zn stearate/Mo stearate, Zn (neodecanoate-naphthenate)/Mo (neodecanoate-naphthenate), Zn (neodecanoate-resinate)/Mo (neodecanoate-resinate), Zn (resinate-naphthenate)/Mo (resinate-naphthenate), Zn (neodecanoate-naphthenate)/Mo naphthenate, Zn (tallate-naphthenate)/Mo naphthenate, Zn (stearate-naphthenate)/Mo naphthenate, Zn (neodecanoate-naphthenate)/Mo neodecanoate, Zn (neodecanoate-resinate)/Mo resinate, Zn (naphthenate-resinate)/Mo resinate, Ni naphthenate/Mo naphthenate, Ni neodecanoate/Mo neodecanoate, Ni stearate/Mo stearate, Ni (neodecanoate-naphthenate)/Mo (neodecanoate-naphthenate), Ni (neodecanoate-resinate)/Mo (neodecanoate-resinate), Ni (resinate-naphthenate)/Mo (resinate-naphthenate), Ni (neodecanoate-naphthenate)/Mo naphthenate, Ni (tallate-naphthenate)/Mo naphthenate, Ni (stearate-naphthenate)/Mo naphthenate, Ni (neodecanoate-naphthenate)/Mo neodecanoate, Ni (neodecanoate-resinate)/Mo resinate, Ni (naphthenate-resinate)/Mo resinate, Co naphthenate/Mo naphthenate, Co neodecanoate/Mo neodecanoate, Co stearate/Mo stearate, Co (neodecanoate-naphthenate)/Mo (neodecanoate-naphthenate), Co (neodecanoate-resinate)/Mo (neodecanoate-resinate), Co (resinate-naphthenate)/Mo (resinate-naphthenate), Co (neodecanoate-naphthenate)/Mo naphthenate, Co (tallate-naphthenate)/Mo naphthenate, Co (stearate-naphthenate)/Mo naphthenate, Co (neodecanoate-naphthenate)/Mo neodecanoate, Co (neodecanoate-resinate)/Mo resinate, Co (naphthenate-resinate)/Mo resinate, Ti naphthenate/Mo naphthenate, Ti neodecanoate/Mo neodecanoate, Ti (neodecanoate-naphthenate)/Mo (neodecanoate-naphthenate), and Co (neodecanoate-naphthenate)/Mo neodecanoate.

Or, there can be cited metallic soaps comprising 3 or more metals, such as (Zn—Ni) naphthenate/Mo naphthenate, (Zn—Ni) neodecanoate/Mo neodecanoate, (Zn—Ni) stearate/Mo stearate, (Zn—Ni) (neodecanoate-naphthenate/Mo naphthenate, (Zn—Ni) (tallate-naphthenate)/Mo naphthenate, (Zn—Ni) (stearate-naphthenate)/Mo naphthenate, (Zn—Ni) (neodecanoate-naphthenate)/Mo neodecanoate, (Zn—Ni) (neodecanoate-resinate)/Mo resinate, (Zn—Ni) (naphthenate-resinate)/Mo resinate, (Zn—Mg) (neodecanoate-naphthenate)/Mo naphthenate, (Zn—Ni—Co) naphthenate/Mo naphthenate, (Zn—Ni—Co) neodecanoate/Mo neodecanoate, (Zn—Ni—Co) stearate/Mo stearate, (Zn—Ni—Co) (neodecanoate naphthenate)/Mo naphthenate, (Zn—Ni—Co) (tallate-naphthenate)/Mo naphthenate, (Zn—Ni—Co) (stearate-naphthenate)/Mo naphthenate, (Zn—Ni—Co) (neodecanate-naphthenate)/Mo neodecanoate, (Zn—Ni—Co) (neodecanoate-resinate)/Mo resinate, and (Zn—Ni—Co) (naphthenate-resinate)/Mo resinate.

In the practice of the first embodiment of the present invention, first the molybdenum soap must be synthesized under the conditions where the fatty acid is in excess and then the excess fatty acid and the metal compound are reacted to produce a metallic soap other than molybdenum soap. When it is tried to produce a molybdenum soap-containing mixed metallic soap in a reverse order, for example, after a metallic soap different from the molybdenum soap is produced under the conditions where the fatty acid is in excess, a molybdenum salt (for example, ammonium molybdate) is added, it is often the case that no good yield can be obtained.

As the production method for the molybdenum compounds, the methods thus far reported can be used. For example, there can be used the method for producing molybdenum salts including heating a metal oxalate compound selected from the group consisting of compounds of molybdenum having a valence of +6, for example, together with a hydrocarbon carboxylic acid having 4 to 50 carbon atoms (U.S. Pat. No. 3,362,972), the method for producing of a direct reaction of a molybdenum compound at a high temperature while removing water from the reaction mixture (U.S. Pat. No. 3,578,690), the method for heating molybdenum trioxide, oxalic acid, water, and hexanoic acid in the reaction of molybdenum and a carboxylic acid (Japanese Patent Publication No. 42-21326), the method for producing an organomolybdenum compound characterized by reducing an aqueous solution of a compound of molybdenum having a valence of IV in acidic conditions, mixing this with an organic acid or alcohol having a high boiling point and heating the mixture for reaction, and at the same time distilling off water and readily volatile compounds (Japanese Patent Publication No. 51-40059), and the like.

However, in these reactions, the reaction must be performed under the conditions where the fatty acid is in excess.

More particularly, the fatty acid that exists in excess when the molybdenum soap is synthesized also serves a reaction solvent that prevents the solidification of the reaction product, so that its amount gives a great influence on the reaction of molybdenum soap. As the conditions of excessive fatty acid upon synthesizing the molybdenum soap, it is preferred that a molar ratio of the fatty acid to molybdenum is 3/1 or more.

As shown in the embodiments of the present invention, the molar ratio of fatty acid to molybdenum upon synthesizing the molybdenum soap being less than 3/1 increases the amount of residual solids after the reaction no matter how the reaction temperature is elevated or the reaction time is prolonged, so that it is difficult to synthesize the molybdenum soap in good yields. Furthermore, in view of the reactivity of the molybdenum soap, while larger amounts of fatty acid than that of molybdenum are preferred, the molar ratio of the fatty acid to molybdenum of 30/1 or less, preferably 21/1 or less is desirable in view of the use of a mixed soap. For example, when a fatty acid and ammonium molybdate are reacted directly, it is preferred that they are reacted at 240° C. for 6 hours. Although the reaction may be performed at a higher temperature or for a longer time, a temperature of 300° C. or more or a time of 100 hours or more must be avoided since in such a case, heat decomposition is feared.

Upon the synthesis of molybdenum soap, in many cases water is used as disclosed in Japanese Patent Publication No. 42-21326. However, it has the problem that removal of water takes time and the risks of heating at high temperatures in the presence of water. The present inventors have found that in the previously proposed production method (Japanese Patent Application No. 9-92335), the amount of water in the reaction system gives a great influence on the yield and a molybdenum soap can be produced very safely in good yields when it is produced without adding any water. Therefore, to achieve the present invention, water may be added; however, it is preferred that no water be added since without addition of any water, the above-described problems are solved.

Oxalic acid may be used as a reaction accelerator upon synthesizing the molybdenum soap. However, it is preferred to add a reduced amount of oxalic acid or add no oxalic acid in order to reduce the amount of excess fatty acid upon synthesizing the molybdenum soap.

The fatty acid upon synthesizing the molybdenum soap or the metallic soap other than the molybdenum soap may be a single fatty acid or a mixture of two or more fatty acids. The metallic soap other than the molybdenum soap must comprise at least one fatty acid that is the same as the fatty acid of the molybdenum soap. No containment of such a fatty acid that is the same as the fatty acid of the molybdenum soap is essentially impossible in the first embodiment of the present invention where the synthesis of molybdenum soap is carried out under the conditions where the fatty acid is in excess. Further, in many cases, a homogeneous molybdenum soap-containing metallic soap cannot be produced.

The metallic soap other than the molybdenum soap is synthesized by the reaction between the unreacted fatty acid upon synthesizing the molybdenum soap and the metal compound that is added to the reaction system. However, a fatty acid that is the same as or different from the previously existing fatty acid may be freshly added.

The method for producing a metallic soap different from the molybdenum soap to be produced after the fatty acid molybdenum compound is produced is preferably a method in which a metal compound and a fatty acid are reacted directly. Upon the reaction, organic solvents such as alcohols, aromatic and paraffin solvents may be used. However, the reaction without addition of any solvent is desirable in order for the reaction to proceed efficiently. In this case, it is desirable that the metallic soap to be produced, differing from the molybdenum soap, have a softening point of 120° C. or less. When it is 120° C. or more, the viscosity increases according as the reaction proceeds so that the reaction does not proceed efficiently and sometimes the reaction stops. In the presence of the molybdenum soap, the reaction temperature upon synthesizing the metallic soap different from the molybdenum soap, which may depend on the amount of the molybdenum soap and that of the metallic soap differing from the molybdenum soap, is advantageously 70 to 200° C., preferably 120 to 190° C., so that the reaction can proceed efficiently.

The addition amount of the metal compound other than molybdenum, which may depend on the amount of the fatty acid, is desirably 1 to 4 folds, preferably 1.1 to 2 folds the amount equivalent to the fatty acid, in view of reaction efficiency. When the addition amount of the metal compound is too small, sometimes the fatty acid cannot be removed completely while when it is too large, removal of the unreacted metal compound takes a long time. The unreacted metal compound can be removed by filtration or similar like operation.

Use of the molybdenum soap not containing the fatty acid in excess alone results in a high softening point, and the reaction with the metal compound or mixing with the metallic soap other than the molybdenum soap is difficult. The reason why a homogeneous molybdenum soap-containing metallic soap can be produced in good yields would be presumed that as a result of the production of a molybdenum soap under the conditions where the amount of the fatty acid is in excess, also taking into account of the amount required for the reaction with the metallic soap other than the molybdenum soap, the reaction can switch over to the second stage, i.e., the synthetic reaction for the metallic soap other than the molybdenum soap in a state where the molybdenum soap is homogeneously dissolved in the fatty acid, so that the fluctuation of the metal component is small. Further, this would be considered to be attributable to the fact that the fatty acid serving as the reaction solvent is consumed as the reaction proceeds while the metallic soap produced through the reaction having a softening point lower than that of the molybdenum soap in turn has an effect of decreasing the softening point of the total composition so that the mixture can be stirred even as the reaction proceeds, and the fatty acid and metal compound are reacted efficiently until the completion of the reaction. Since the reaction can be completed under relatively low temperature conditions and in a short period of time, the effect of inhibiting side reactions and economical effect, etc. can be expected.

In the first embodiment of the present invention, as described above, if the order of the reaction steps is that after the metallic soap differing from the molybdenum soap is produced under the conditions where the fatty acid is in excess, a molybdenum salt is added to produce a mixed metallic soap containing the molybdenum soap, good yields cannot be expected in many cases. Furthermore, in this case, the metallic soap other than molybdenum soap comprises one or more fatty acid moieties that are the same as those of the molybdenum soap. However, in the second embodiment of the present invention, selective use of a metallic soap having a softening point of 120° C. or less as the metallic soap other than the molybdenum soap enables the achievement of good yields, though somewhat decreased, even in the above-described order of reaction. In this case, the metallic soap other than the molybdenum soap may be constituted by a fatty acid other than that of the molybdenum soap.

Hereafter, the second embodiment will be explained.

The metallic soap having a softening point of 120° C. or less used in the second embodiment of the present invention includes metallic soaps synthesized from oxides, hydroxides, carbonates, alkoxides, organometallic compounds, etc. of metals such as magnesium, calcium, strontium, barium, zinc, cadmium, nickel, titanium, aluminum, etc. and a fatty acid. More specifically, zinc naphthenate, zinc neodecanoate, nickel naphthenate, nickel neodecanoate, magnesium tallate, etc. Of course, two or more of them may be used in combination. Therefore, the fatty acid capable of forming a metallic soap having a softening point of 120° C. or less includes naphthenic acid, neodecanoic acid, tallate, etc. To synthesize a homogeneous molybdenum-containing metallic soap with good reactivity, though depending on what properties are desired, use of a zinc soap, a nickel soap, or a cobalt soap is preferred.

Use of metallic soaps having a softening point above 120° C. will increase the viscosity at the final stage of the reaction upon synthesizing the molybdenum soap so that the reaction is difficult to be completed. The softening point of the metallic soap that coexists upon synthesizing the molybdenum soap is preferably as low as possible in view of the proceeding of the reaction. However, to give an influence on the softening point of the molybdenum metallic soap, it is preferred a from practical viewpoint that the softening point be 20° C. or more, more preferably 30° C. or more.

In the second embodiment of the present invention, the atomic ratio of the molybdenum to the metal other than molybdenum contained in the molybdenum soap-containing metallic soap is preferably ½ or less. If the ratio is above ½, decreases in the softening point and viscosity are insufficient upon synthesizing the molybdenum soap so that the reaction is difficult to proceed.

The fatty acid used in the second embodiment of the present invention includes natural or synthetic, saturated or unsaturated fatty acids having a backbone chain having from 6 to 30 carbon atoms or mixtures thereof. Specific examples thereof include caproic acid, caprylic acid, capric acid, lauric acid, myristic acid, palmitic acid, stearic acid, isostearic acid, arachic acid, behenic acid, oleic acid, linoleic acid, linolenic acid, ricinoleic acid, 12-hydroxystearic acid, dimeric acid, tallate, naphthenic acid, neodecanoic acid, resin acid or natural oil and fat fatty acids containing these as main components, for example, fish oil hardened fatty acids, beef tallow hardened fatty acids, etc.

The molybdenum compound that is used in the second embodiment in the present invention includes molybdenum oxide, ammonium molybdate, sodium molybdate, molybdenum acetylacetonate, etc.

The molybdenum soap is a soap that can be formed from the above-described fatty acids and molybdenum and specific examples thereof include molybdenum naphthenate, molybdenum neodecanoate, molybdenum resinate, etc.

The molybdenum soap-containing metallic soap that can be produced according to the second embodiment of the present invention includes the following compounds.

The metallic soaps comprising two metals include, for example, Zn naphthenate/Mo naphthenate, Ni naphthenate/Mo naphthenate, Co naphthenate/Mo naphthenate, Zn neodecanoate/Mo naphthenate, Ni neodecanoate/Mo naphthenate, Co neodecanoate/Mo naphthenate, Zn neodecanoate/Mo neodecanoate, (Zn/Mo) (neodecanoate-naphthenate), (Zn/Mo) (neodecanoate-resinate), (Zn/Mo) (resinate-naphthenate), Zn (neodecanoate-naphthenate)/Mo naphthenate, Zn (tallate-naphthenate)/Mo naphthenate, Zn (stearate-naphthenate)/Mo naphthenate, Zn (neodecanoate-naphthenate)/Mo neodecanoate, Zn (neodecanoate-resinate) /Mo resinate, Zn (naphthenate-resinate)/Mo resinate, Ni naphthenate/Mo naphthenate, Ni neodecanoate/Mo neodecanoate, Ni stearate/Mo stearate, (Ni/Mo) (neodecanoate-naphthenate), (Ni/Mo) (neodecanoate-resinate), (Ni/Mo) (neodecanoate-naphthenate), Ni (neodecanoate-naphthenate)/Mo naphthenate, Ni (tallate-naphthenate)/Mo naphthenate, Ni (stearate-naphthenate)/ Mo naphthenate, Ni (neodecanoate-naphthenate)/Mo neodecanoate, Ni (neodecanoate-resinate)/Mo resinate, Ni (naphthenate-resinate)/Mo resinate, Co naphthenate/Mo naphthenate, Co neodecanoate/Mo neodecanoate, Co stearate/Mo stearate, (Co/Mo) (neodecanoate-naphthenate), (Co/Mo) (neodecanoate-resinate), (Co/Mo) (neodecanoate-resinate), Co (neodecanoate-naphthenate)/Mo naphthenate, Co (tallate-naphthenate)/Mo naphthenate, Co (stearate-naphthenate)/Mo naphthenate, Co (neodecanoate-naphthenate)/Mo neodecanoate, Co (neodecanoate-resinate)/Mo resinate, Co (naphthenate-resinate)/Mo resinate, Ti naphthenate/Mo naphthenate, Ti neodecanoate/ Mo neodecanoate, (Ti/Mo) (neodecanoate-naphthenate), and Co (neodecanoate-naphthenate/Mo neodecanoate.

The metallic soaps comprising three or more metals include, for example, (Zn—Ni) naphthenate/Mo naphthenate, (Zn—Ni) neodecanoate/Mo neodecanoate, (Zn—Ni) stearate/Mo stearate, (Zn—Ni) (neodecanoate-naphthenate/Mo naphthenate, (Zn—Ni) (tallate-naphthenate)/Mo naphthenate, (Zn—Ni) (stearate-naphthenate)/Mo naphthenate, (Zn—Ni) (neodecanoate-naphthenate)/Mo neodecanoate, (Zn—Ni) (neodecanoate-resinate)/Mo resinate, (Zn—Ni) (naphthenate-resinate)/Mo resinate, (Zn—Mg) (neodecanoate-naphthenate)/Mo naphthenate, (Zn—Ni—Co) naphthenate/Mo naphthenate, (Zn—Ni—Co) neodecanoate/Mo neodecanoate, (Zn—Ni—Co) stearate/Mo stearate, (Zn—Ni—Co) (neodecanoate naphthenate)/Mo naphthenate, (Zn—Ni—Co) (tallate-naphthenate)/Mo naphthenate, (Zn—Ni—Co) (stearate-naphthenate)/Mo naphthenate, (Zn—Ni—Co) (neodecanoate-naphthenate)/Mo neodecanoate, (Zn—Ni—

Co) (neodecanoate-resinate)/Mo resinate, (Zn—Ni—Co) (naphthenate-resinate)/Mo resinate, etc.

In the second embodiment of the present invention, the reaction between the molybdenum compound and the fatty acid must be performed in the presence of the metallic soap having a softening point of 120° C. or less or while synthesizing that metallic soap. When in a reverse order, for example, the molybdenum soap is synthesized first, the viscosity increases as the reaction proceeds and, as the case may be, solidification occurs so that the reaction is not completed, thus failing to produce a molybdenum soap-containing metallic soap homogeneously or in good yields.

Generally, the reactivity between the molybdenum compound and fatty acid is low and hence when the reaction is initiated by simultaneously adding the molybdenum compound and the metal compound other than molybdenum compound and fatty acid, the reaction of the metal compound other than the molybdenum compound proceeds earlier so that there occurs no problem in the production of a metallic soap having a low softening point. As the case may be, the temperature program will be effective that the reaction is initiated at 180° C. or less to first produce a metallic soap having a low softening point and the temperature is elevated at 200° C. or more upon synthesizing the molybdenum soap. Furthermore, a metallic soap having a low softening point may be added after the reaction between the molybdenum compound and fatty acid is allowed to proceed to some extent.

The method for producing the molybdenum compound to be used in the present invention may be the method described in the first embodiment. However, preferably, use of compounds having a strong oxidizing or reducing ability such as a large amount of oxalic acid is avoided since there is a fear that the metallic soap synthesized or prepared in the preceding step could be decomposed therewith.

In some cases, oxalic acid is used upon synthesizing the molybdenum soap. However, since it decomposes the metallic soap that is synthesized before the molybdenum soap is produced, it is advisable in the present invention that its amount be reduced or use of it be avoided. When the usage of oxalic acid is large, sometimes the metallic soap will be decomposed and the amount of residual solids after the reaction will increase.

The fatty acid to be used upon synthesizing the molybdenum soap or the metallic soap having a softening point of 120° C. or less may be a single fatty acid or a mixture of two or more fatty acids.

A method for producing the metallic soap having a softening point of 120° C. or less is preferably the method in which the metal compound and fatty acid are reacted directly. Upon the reaction, organic solvents such as alcohols, aromatic solvents or paraffin solvents may be used. However, the reaction without addition of any solvent is desirable in order for the reaction to proceed efficiently.

Use of the molybdenum soap alone results in a high softening point and the reaction with the metal compound or mixing with the metallic soap other than the molybdenum soap is difficult. The reason why a molybdenum soap-containing metallic soap that is homogeneous in metal component can be produced in good yields by the second embodiment of the present invention would be presumed that the metallic soap having a low softening point is used as a reaction solvent, so that the reaction mixture can be stirred until the completion of the reaction.

BEST EMBODIMENTS FOR CARRYING OUT THE INVENTION

Hereafter, the present invention will be explained more specifically by examples and comparative examples. The syntheses were all carried out in a nitrogen atmosphere. The progress of the reaction was judged by the amount of the toluene-insoluble portion since the molybdenum compounds and metal compounds were insoluble in toluene.

EXAMPLE 1

14.7 g (0.012 mol, Mo 0.083 mol) of ammonium molybdate $((NH_4)_8Mo_7O_{24}4H_2O)$ and 82.8 g (0.333 mol) of naphthenic acid were mixed in a 500-ml flask and stirred under heating for 6 hours at an oil temperature of 240° C. while removing the volatile components. Thereafter, 127.9 g (0.748 mol) of neodecanoic acid and 40.6 g (0.499 mol) of zinc oxide were added thereto and the mixture was stirred under heating for 2 hours at an oil temperature of 160° C. while removing the volatile components. Subsequently, the mixture was dried under reduced pressure for 2 hours at an oil temperature of 160° C. at 20 mmHg to obtain 251.5 g of a composite soap of Zn (naphthenate-neodecanoate) (3/9)/ Mo naphthenate (Zn/Mo (molar ratio)=6/1). The toluene-insoluble portion was 0.1% or less based on the obtained molybdenum soap-containing metallic soap.

EXAMPLE 2

The procedures of Example 1 were repeated except that the molar ratio of (naphthenic acid/molybdenum) was changed to (3/1) to produce a composite metallic soap containing molybdenum. The toluene-insoluble portion was 0.1% or less based on the obtained molybdenum soap-containing metallic soap.

EXAMPLE 3

The procedures of Example 1 were repeated except that the molar ratio of (naphthenic acid/molybdenum) was changed to (7/1) to produce a composite metallic soap containing molybdenum. The toluene-insoluble portion was 0.1% or less based on the obtained molybdenum soap-containing metallic soap.

EXAMPLE 4

The procedures of Example 1 were repeated except that the molar ratio of (naphthenic acid/molybdenum) was changed to (2/1) and the reaction conditions of the molybdenum soap were changed to 240° C. for 12 hours to produce a composite metallic soap containing molybdenum. The toluene-insoluble portion was 0.8% based on the obtained molybdenum soap-containing metallic soap.

EXAMPLE 5

The procedures of Example 1 were repeated except that the molar ratio of (naphthenic acid/molybdenum) was changed to (2/1) and the reaction conditions of the molybdenum soap were changed to 260° C. for 12 hours to produce a composite metallic soap containing molybdenum. The toluene-insoluble portion was 0.5% based on the obtained molybdenum soap-containing metallic soap.

EXAMPLE 6

The procedures of Example 1 were repeated except that the molar ratio of (naphthenic acid/molybdenum) was changed to (7/1) and oxalic acid was added by 0.5 equivalent relative to molybdenum to produce a composite metallic soap containing molybdenum. The toluene-insoluble portion was 0.4% based on the obtained molybdenum sopa-containing metallic soap.

The results obtained are shown in the table below.

TABLE 1

Experimental Results on Zn (Neodecanoate-Naphthenate)/Mo Naphthenate System

| | Example 1 | Example 2 | Example 3 | Example 4 | Example 5 | Example 6 |
|---|---|---|---|---|---|---|
| Naphthenic acid/molybdenum (molar ratio) | 4/1 | 3/1 | 7/1 | 2/1 | 2/1 | 7/1 |
| Additional amount of oxalic acid (molar ratio, relative to Molybdenum) | 0 | 0 | 0 | 0 | 0 | 0.5 |
| Molybdenum soap reaction temperature (° C.) | 240 | 240 | 240 | 240 | 260 | 240 |
| Molybdenum soap Reaction time (hour) | 6 | 6 | 6 | 12 | 12 | 6 |
| Toluene-insoluble portion (wt %) | <0.1 | <0.1 | <0.1 | 0.8 | 0.5 | 0.4 |

EXAMPLE 7

Example of synthesizing (molybdenum/zinc) composite soap 153.9 g (0.900 mol) of neodecanoic acid, 12.2 g (0.010 mol, Mo 0.069 mol) of ammonium molybdate ($(NH_4)_8Mo_7O_{24}4H_2O$), and 33.8 g (0.415 mol) of zinc oxide were mixed in a 500-ml flask, and the mixture was stirred under heating for 10 hours at an oil temperature of 240° C. while removing the volatile components. Thereafter, the mixture was dried under a reduced pressure for 2 hours at an oil temperature of 160° C. at 20 mmHg to obtain 187.7 g of a composite soap of (Zn/Mo) (6/1) neodecanoate. The toluene-insoluble portion of the resulting Zn neodecanoate/Mo neodecanoate was less than 1% based on the obtained molybdenum soap-containing metallic soap.

EXAMPLE 8

20.3 g (0.016 mol, Mo 0.115 mol) of ammonium molybdate, and 28.6 g (0.115 mol) of naphthenic acid were charged in a 500-ml flask and when the temperature reached 240° C., Zn neodecanoate, which had been prepared by charging 237.3 g (1.388 mol) of neodecanoate and 56.5 g (0.694 mol) of zinc oxide in another 500-ml flask and heating at 160° C. for 40 minutes while stirring, was added, and further the ammonium molybdate and naphthenic acid were reacted at 240° C. for 10 hours. The toluene-insoluble portion of the resulting Zn neodecanoate/Mo naphthenate was less than 1% based on the obtained molybdenum soap-containing metallic soap.

COMPARATIVE EXAMPLE 1

20.3 g (0.016 mol, Mo 0.115 mol) of ammonium molybdate, and 28.6 g (0.115 mol) of naphthenic acid were charged in a 500-ml flask and reacted at 240° C. for 40 hours. To this, Zn neodecanoate, which had been synthesized from 237.3 g (1.388 mol) of neodecanoate and 56.5 g (0.694 mol) of zinc oxide in another 500-ml flask and stirred under heating at 160° C. for 40 minutes, was added and the mixture was mixed under heating at 180° C. for 2 hours. The mixing of Mo naphthenate and Zn neodecanoate had insufficient since the Mo naphthenate was solidified and could not be stirred, and the obtained metallic soap was not homogeneous. The toluene-insoluble portion of the resulting Zn neodecanoate/Mo naphthenate was 7.0% based on the obtained molybdenum soap-containing metallic soap.

COMPARATIVE EXAMPLE 2

The procedures of Example 5 were repeated except that the molar ratio of Mo/Zn was changed to 0.6 to synthesize a (Zn/Mo) neodecanoate soap. The toluene-insoluble portion of the obtained (Zn/Mo) neodecanoate was 5.0% based on the obtained molybdenum soap-containing metallic soap.

EXAMPLE 9

150.0 g (0.877 mol) of neodecanoic acid, 11.9 g (0.010 mol, Mo 0.067 mol) of ammonium molybdate ($(NH_4)_8Mo_7O_{24}4H_2O$), 4.3 g (0.034 mol) of oxalic acid, and 33.0 g (0.40 mol) of zinc oxide were mixed in a 500-ml flask, and the mixture was stirred under heating at an oil temperature of 240° C. for 10 hours while removing the volatile components. Thereafter, the mixture was dried under a reduced pressure for 2 hours at an oil temperature of 160° C. at 20 mmHg to obtain a composite soap of (Zn/Mo) (6/1) neodecanoate. The toluene-insoluble portion thereof was 3.0%.

INDUSTRIAL APPLICABILITY

As described above, according to the present invention, a homogeneous molybdenum soap-containing metallic soap can be produced in good yields. The molybdenum soap-containing metallic soap produced by the present invention are useful as an adhesive for accelerating the adhesion between a steel cord for radial tires and rubber, a hardener of an unsaturated polyester resin, a hardening promoter for paints, a lubricant, a petroleum additive, catalysts for various chemical reactions, etc.

What is claimed is:

1. A method for producing a molybdenum soap-containing metallic soap, comprising the steps of reacting a fatty acid and a molybdenum compound under conditions where the fatty acid is in excess to synthesize a molybdenum soap and then adding an inorganic metal compound other than the molybdenum compound for reaction with the excess amount of fatty acid.

2. The method for producing a molybdenum soap-containing metallic soap as claimed in claim 1, characterized in that no oxalic acid is added, and the fatty acid and the molybdenum compound are reacted directly at a fatty acid-to-molybdenum molar ratio of 3/1 or more to synthesize a fatty acid molybdenum soap.

3. A method for producing a molybdenum soap-containing metallic soap, comprising the steps of reacting a molybdenum compound and a fatty acid in the presence of a fatty acid and an inorganic metal compound other than molybdenum compound that form a metallic soap having a softening point of 120° C. or less.

4. A method for producing a molybdenum soap-containing metallic soap, comprising the steps of synthesizing a molybdenum soap in the presence of a metallic soap having a softening point of 120° C. or less.

5. The method for producing a molybdenum soap-containing metallic soap as claimed in claim 3, characterized by comprising synthesizing the molybdenum soap without addition of any oxalic acid.

6. The method for producing a molybdenum soap-containing metallic soap as claimed in claim 3, characterized in that the atomic ratio of the molybdenum to the inorganic metal other than molybdenum which are contained in the molybdenum soap-containing metallic soap is ½ or less.

7. The method for producing a molybdenum soap-containing metallic soap as claimed in claim 4, characterized by comprising synthesizing the molybdenum soap without addition of any oxalic acid.

8. The method for producing a molybdenum soap-containing metallic soap as claimed in claim 4, characterized in that the atomic ratio of the molybdenum to the inorganic metal other than molybdenum which are contained in the molybdenum soap-containing metallic soap is ½ or less.

* * * * *